United States Patent [19]

Link et al.

[11] Patent Number: 5,185,321

[45] Date of Patent: Feb. 9, 1993

[54] PROCESS FOR PRODUCING IMMUNOSTIMULANTS

[75] Inventors: Harriet Link, Vevey; Jean-Jacques Pahud, Mont-Pelerin, both of Switzerland

[73] Assignee: Nestec S.A., Vevey, Switzerland

[21] Appl. No.: 619,119

[22] Filed: Nov. 27, 1990

[30] Foreign Application Priority Data

Dec. 13, 1989 [CH] Switzerland .................. 4484/89

[51] Int. Cl.⁵ .................. A61K 37/18; C07K 1/12; C12P 21/06; A23C 21/08
[52] U.S. Cl. .................................. 514/8; 426/43; 435/68.1; 514/885; 530/322; 530/825
[58] Field of Search ............. 530/322, 825; 426/43; 514/885, 19, 8; 435/68.1

[56] References Cited

U.S. PATENT DOCUMENTS

| | | | |
|---|---|---|---|
| 3,762,998 | 10/1973 | Bogdanov | 435/71.3 |
| 4,501,693 | 2/1985 | d'Hinterland et al. | 435/259 |
| 4,515,891 | 5/1985 | Yokegawa et al. | 435/220 |

FOREIGN PATENT DOCUMENTS

| | | | |
|---|---|---|---|
| 2710455 | 9/1977 | Fed. Rep. of Germany | 530/322 |
| 53298 | 4/1980 | Japan | 435/68.1 |
| 618088 | 8/1978 | U.S.S.R. | |
| 789096 | 12/1980 | U.S.S.R. | 426/43 |
| 1465003 | 3/1989 | U.S.S.R. | 426/43 |
| 2046759A | 11/1980 | United Kingdom . | |

OTHER PUBLICATIONS

Pahud et al, "Calf rennet lysozyme" *Biochem. J.*, vol. 201, 1982, pp. 661–664.

Kuwana, et al. "Effect of Lytic Enzyme on Protoplast Formation of Lactic Acid Bacteria" Seikatsu Eisei (Life and Hygiene), vol. 31(2) 1987, pp. 32–41 (with translation).

Neviani, et al., "Sensitivity of Lactic Bacteria to Lysozyme" L'Industria del latte 24(1), 1988 (with translation).

Nomoto, et al. "Augmentation of resistance of mice to bacterial infection by a polysaccharide-peptidoglycan complex (PSPG) extracted from Lactobacillus casei", *Biotherapy.* 1:169–177, 1989.

*Primary Examiner*—Jeffrey E. Russel
*Attorney, Agent, or Firm*—Vogt & O'Donnell

[57] ABSTRACT

Immunostimulant products are prepared by adding lysozyme to a culture of *L.bulgaricus* at a pH of from 4–8 and then incubating the culture to hydrolyze peptidoglycans of cell walls of the bacteria. A suspension containing the lysozyme-treated *L.bulgaricus* is collected, which is centrifuged to obtain an immunostimulant supernatant. The supernatant may be filtered to obtain an immunostimulant solution, which may be added to a fermented milk, or to a whey, to prepare an immunostimulant product. Alternatively, *L.bulgaricus* may be cultured and hydrolyzed by lysozyme in a milk product to provide an immunostimulant milk product.

32 Claims, No Drawings

PROCESS FOR PRODUCING IMMUNOSTIMULANTS

BACKGROUND OF THE INVENTION

This invention relates to an immunostimulant, to a process for its production and to the use of the immunostimulant and/or the process in the field of fermented milks.

It is known that an anticarcinogenic agent can be produced by a process comprising the steps of cultivating a lactobacillus, particularly *Lactobacillus bulgaricus*, hydrolyzing the lactobacillus with a proteolytic enzyme and extracting from the hydrolyzate a product rich in protein and ribonucleic acid which shows anticarcinogenic activity.

In addition, it is known that a milk-based dietetic product for infants can be produced by a process in which a milk acidified by *Lactobacillus acidophilus* is supplemented with oligoelements, vitamins and a lysozyme solution. The lysozyme solution is intended to replace the lysozyme present in maternal milk and to improve the keeping qualities, the taste and the texture of this dietetic product.

SUMMARY OF THE INVENTION

The object of the present invention is to provide an effective immunostimulant which can be obtained from a lactic bacterium and which is particularly suitable for use in the field of fermented milks.

To this end, the immunostimulant according to the invention comprises N-acetyl muramyl peptides derived by hydrolysis with lysozyme from peptidoglycans from the cell wall of lactic bacteria sensitive to lysozyme, particularly *Lactobacillus bulgaricus*.

In the context of the invention, "lactic bacteria sensitive to lysozyme" means lactic bacteria of which the cell walls comprises peptidoglycans hydrolyzable by lysozyme, i.e., degradable into N-acetyl muramyl peptides under the effect of lysozyme.

In the process for the production of an immunostimulant according to the present invention, the peptidoglycans from the cell wall of lactic bacteria sensitive to lysozyme, particularly *Lactobacillus bulgaricus*, are hydrolyzed with lysozyme to derive N-acetyl muramyl peptides therefrom. It has been found that an agent of the type in question has a remarkable stimulating effect on the immune response, particularly on the immune response to gram-negative enteropathogenic bacteria, such as *E. coli* for example.

The immunostimulant according to the invention is particularly suitable for use in a fermented milk, particularly in a yoghurt or in a whey product.

Similarly, the process according to the invention is suitable for use, i.e. may be directly carried out, in the production of a fermented milk, particularly a yoghurt, or in the production of a whey product.

Accordingly, the present invention also relates to these uses.

DETAILED DESCRIPTION OF THE INVENTION

In the context of the invention, the immunostimulant effect of the product according to the invention is qualitatively estimated in tests on mice. It is known that, although the results of such tests cannot be directly applied to man, they nonetheless provide useful information.

The process according to the invention may be carried out using a pure culture or suspension of a lactic bacterium sensitive to lysozyme or a mixed culture or suspension comprising bacteria sensitive and non-sensitive to lysozyme. It is possible in particular to use a pure culture of *Lactobacillus bulgaricus* or a mixed culture of *Lactobacillus bulgaricus* and *Streptococcus thermophilus*, i.e. a yoghurt culture, for example of the commercially available type.

More particularly, it is possible to use a culture or a suspension containing $10^6$–$10^{10}$ cells of lactic bacterium sensitive to lysozyme per ml. To produce a desired quantity of cells in a sufficient concentration, a suitable culture medium may be inoculated with a seed culture of the bacterium in question and incubated at a temperature and at a pH favourable to the growth of the bacterium over a period of time sufficient to re-establish in the culture medium a concentration of cells comparable with that of the starting culture. The culture medium may be, for example, a milk-based medium, such as skimmed or unskimmed cow's milk, a whey, an ultrafiltration permeate, or a synthetic medium.

A culture of *L. bulgaricus* is preferably used. To prepare this culture, a cow's milk or a synthetic medium, such as the MRS medium (Difco) for example, may be inoculated with a seed culture of this microorganism and incubated for 3–6 h at 37°–45° C. If the culture is incubated for less than 3 h or at a temperature below 37° C., it is in danger of remaining in so-called latent phase, i.e. the starting phase of multiplication of the microorganism, or of not being involved long enough in the so-called exponential phase, i.e. the phase of exponential multiplication of the microorganism.

On the other hand, if the culture is incubated for more than 6 h, it is in danger of entering the stationary phase, i.e. the phase in which multiplication of the microorganisms stops and during which the composition of the cell wall can change unfavourably. Finally, beyond 45° C., the temperature is no longer favourable to the growth of *L. bulgaricus*.

The hydrolysis step is then carried out with lysozyme. The lysozyme may emanate from any suitable source, more particularly from rennet, particularly ruminant (above all bovine) rennet, or from egg white, optionally in pure form. In one particular embodiment of the process according to the invention, the rennet is used as such, i.e. without the lysozyme separated therefrom.

The peptidoglycans from the cell wall of the lactic bacteria mentioned may be hydrolyzed for 1 to 48 h and preferably for 12 to 24 h at 15° to 37° C. using 1 to 500 µg lysozyme per ml of a culture containing $10^6$ to $10^{10}$ cells of these bacteria per ml, for example at a pH value favourable to the action of the lysozyme used. This pH is of the order of 4 to 6 for a lysozyme of rennet and of the order of 6 to 8 for a lysozyme of egg white for example.

For the uses according to the invention, it is possible on the one hand to add the immunostimulant either as such or in the form of an aqueous extract to a fermented milk, such as a liquid or stirred yoghurt, or to a whey product, such as a whey-based beverage. The quantity of agent added may correspond, for example, to the quantity of N-acetyl muramyl peptides derived from the walls of $10^6$–$10^{10}$ cells of lactic bacteria sensitive to lysozyme per ml of said fermented milk or said whey product.

On the other hand, the hydrolysis step may be carried out, for example, in a fermented milk, more particularly in a milk fermented by L. bulgaricus on its own or in combination with S. thermophilus, or in a lactoserum. In the case of the fermented milk, the lysozyme may be added to the milk before, during or after its fermentation, for example in a quantity of approximately 1 to 500 µg lysozyme per ml milk. In the case of whey, the above-mentioned bacteria sensitive to lysozyme may be added to the whey or, where appropriate, may even be cultivated thereon and, if necessary, lysozyme may be added.

EXAMPLES

The invention is illustrated by the following Examples in which percentages are by weight, unless otherwise indicated.

The immunostimulating effect, i.e. the stimulating effect on the immune response, is estimated by determination of concentrations of specific antibodies in mice by the ELISA test.

The ELISA test, which is well known to the expert, comprises detecting an enzyme marking an anti-antibody which attaches itself to a specific antibody of an immunoglobulin, such as IgG, IgM or IgA, which in turn attaches itself to an antigen, such as a bacterial antigen for example, which is itself fixed to a support insoluble in aqueous medium.

EXAMPLE 1

A synthetic culture medium is prepared, consisting of a modified MRS medium (Difco Lab., USA) which has the following composition (expressed in g dry matter per liter medium):

| | |
|---|---|
| Protein hydrolyzate | 10 |
| Meat extract | 10 |
| Yeast extract | 5 |
| Glucose | 20 |
| Lactose | 10 |
| Emulsifier | 1 |
| Ammonium citrate | 2 |
| Sodium acetate | 5 |
| $MgSO_4$ | 0.1 |
| $MnSO_4$ | 0.05 |
| $K_2HPO_4$ | 2 |

This synthetic culture medium has a pH of 6.5. It is sterilized for 15 mins. at 121° C. and then inoculated with a seed culture of Lactobacillus bulgaricus, in the present case a culture of L. bulgaricus NCDO 1489 (National Collection of Food Bacteria, AFRC Institute of Food Research, Reading Laboratory, Shinfield, Reading, RG2 9AT, UK).

The culture is incubated for 6 h at 40° C. The biomass is separated, washed and divided into 2 parts A and B. Part A is suspended in a 0.02 M phosphate buffer at pH 7 while part B is suspended in a 0.01 M acetate buffer at pH 5 in a quantity of $2.10^9$ cells of the microorganism per ml.

The L. bulgaricus cells of suspension A are hydrolyzed with a commercially available lysozyme from egg white (Calbiochem, Federal Republic of Germany). The L. bulgaricus cells of suspension B are hydrolyzed with a rennet lysozyme extracted and purified as described by J. J. Pahud et al., in Biochem. J. 201, 661-664 (1982).

To this end, 16 µg lysozyme are added per ml suspension and incubated for 18 h at 25° C. The suspension is then centrifuged and the supernatant phase is filtered through a membrane having 0.45 µm diameter pores.

Two immunostimulants A and B are thus obtained in the form of sterile solutions or extracts containing the N-acetyl muramyl peptides derived from the cell walls of $2.10^9$ L. bulgaricus cells per ml by hydrolysis with lysozyme from egg white (A) or from rennet (B).

The immunostimulating effect of the agents A and B is determined in mice of the "Swiss white" species (Tuttlingen, Federal Republic of Germany) using the following experimental procedure:

Six groups numbered 1 to 6 each comprising six mice weighing 18-20 g are given a normal diet and water ad lib. Starting from the beginning of the test on day 0, oral intubations are carried out on days 1, 3, 5, 15, 17, 19 and 30. The food and the water are removed from the mice 3 h before each of these intubations and are returned immediately afterwards. Sera are taken from the mice on days 0, 29 and 40. Intestinal washing is carried out on day 40.

Each oral intubation is carried out with a dose of 0.5 ml per mouse. The composition of these doses is the same for the mice of the same group, but varies from group to group in accordance with Table I below. In Table I, the word vaccine" indicates that $5.10^9$ cells of Eschericia coli 0111:K58 have been suspended per dose, one half of the cells having been inactivated for 1 h at 100° C. and the other half having been inactivated with a 0.05% solution of glutaraldehyde (Hilpert et al., Food and Immunology, 1977, Ed. L. Hambraeux, L. A. Hanson, H. McFarlane, Swedish Nutrition Foundation Symposium XIII, 182-196). The letters CT stand for cholera toxin, an immunostimulant well known to the expert. The expression "physiological solution" stands for distilled water containing 0.9% NaCl.

TABLE I

| | | Substances added | |
|---|---|---|---|
| Group | Basic liquid | $NaHCO_3$ % | Others |
| 1 | Physiological solution | 3 | — |
| 2 | " | 3 | 1 µg CT |
| 3 | " | 3 | Vaccine |
| 4 | " | 3 | Vaccine  1 µg CT |
| 5 | Immunostimulant A | 3 | Vaccine |
| 6 | Immunostimulant B | 3 | Vaccine |

The concentration of IgG and IgM antibodies in the sera and the concentration of IgG and IgA antibodies in the intestinal washing fluids taken from the mice are determined by the ELISA test. Table II below shows the relative values obtained. The figures shown are a geometric mean of the values determined for each of the six mice of one and the same group. The asterisks indicate that, for the figures thus marked, the probability that an error has been made in claiming they are different from the corresponding figure (same column) of group 3 (control, mice which have only been given the vaccine) is less than 5%. In other words, for the figures marked with an asterisk, the value "p", determined by unilateral variance analysis, is smaller than 0.05.

TABLE II

| Group | Ex sera: IgG d29 | IgG d40 | IgM d29 | IgM d40 | Ex intestinal fluid: IgG d40 | IgA d40 |
|---|---|---|---|---|---|---|
| 1 | 69 | 57 | 36 | 39 | 8 | 8 |
| 2 | 96 | 94 | 25 | 80 | 10 | 11 |
| 3 | 189 | 489 | 31 | 83 | 11 | 18 |
| 4 | 572* | 759 | 113 | 123* | 13 | 24 |
| 5 | 525* | 828 | 104 | 141* | 18 | 53* |
| 6 | 397* | 1362* | 39 | 45 | 24* | 72* |

It can be seen that the sera removed on days 29 and 40 show an increase by a factor of approximately 2–3 in the concentration of IgG antibodies for the mice which were given the vaccine and immunostimulant A or B (invention, groups 5 and 6) or CT (comparison, group 4) in relation to the mice which were only given the vaccine (control, group 3). By contrast, an increase in the concentration of IgM antibodies is only observed for immunostimulant A (invention, group 5 and CT (comparison, group 3).

The concentration of IgG and IgA antibodies in the intestinal fluids of the mice given the vaccine and immunostimulant A or B (invention, groups 5 and 6) also shows a very distinct increase in relation to that of the intestinal fluids of the mice given the vaccine alone (control, group 3).

EXAMPLE 2

A biomass of $L.\ bulgaricus$ is prepared in the same way as described in Example 1. The biomass is suspended in a 0.01 M acetate buffer at pH 5 in a quantity of $1.6.10^9$ cells of the microorganism per ml.

1% Liquid rennet containing 4% lysozyme (Laboratoire Présure Granday, Beaune, France) is added to the suspension, followed by incubation with gentle stirring for 18 h at 25 C. The suspension is then centrifuged and the supernatant phase is filtered through a membrane having 0.45 μm diameter pores.

An immunostimulant C is thus obtained in the form of a sterile solution or extract containing the N-acetyl muramyl peptides derived from the cell walls of $1.6.10^9$ cells of $L.\ bulgaricus$ per ml by hydrolysis with rennet lysozyme in the form of rennet itself.

The immunostimulating effect of immunostimulant C is verified in mice of the "Swiss white" species in a similar manner to Example 1, except that the immunostimulant is not administered to the mice by intubation, but is added to the water which they drink freely in a quantity of 1 part immunostimulant to 50 parts water. Throughout the test, 10 ml lipid per 24 h are placed at the disposal of the mice of which the daily requirement is approximately 4–7 ml.

Four groups of six mice each numbered 1 to 4 are given a normal diet. Two of these groups receive physiological solution ad lib. The other two are given physiological solution to which immunostimulant C has been added. In addition, the mice of two of these groups are also given a vaccine of $E.\ coli$ by oral intubation in a similar manner to that described in the experimental procedure of Example 1. Table III below summarizes the feeding and/or vaccination program for the mice of the various groups.

TABLE III

| Group | Liquid | Intubation |
|---|---|---|
| 1 | Physiological solution | — |
| 2 | Physiological solution + immunostimulant C | — |
| 3 | Physiological solution + immunostimulant C | Vaccine |
| 4 | Physiological solution + immunostimulant C | Vaccine |

The concentration of IgG and IgM antibodies in the sera and the concentration of IgA antibodies in the intestinal washing fluids taken from the mice are determined by the ELISA test. Table IV below shows the relative values obtained.

TABLE IV

| Group | Ex sera IgG d29 | IgG d40 | IgM d29 | IgM d40 | Ex intestinal fluid IgA d40 |
|---|---|---|---|---|---|
| 1 | 77 | 68 | 54 | 101 | 2 |
| 2 | 96 | 78 | 37 | 66 | 3 |
| 3 | 1427 | 1213 | 71 | 94 | 25 |
| 4 | 2365 | 3180* | 219* | 360** | 31 |

*Value "p" = 0.065
**value "p" = 0.014

It can be seen that the sera removed on days 29 and 40 show an increase by a factor of approximately 2–3 or even more in the concentration of IgG and IgM antibodies for the mice which were given the vaccine and which drank water containing immunostimulant C (invention, group 4) in relation to the mice which were given the vaccine alone (control, group 3). By contrast, there is hardly any difference between the concentrations of IgA antibodies for the mice of these groups 3 and 4.

EXAMPLE 3

A cow's milk is inoculated with 3% by volume of a pure commercially available seed culture containing approximately $10^8$ cells of $Lactobacillus\ bulgaricus$ per ml. The culture thus inoculated is then incubated for 5 h at 40° C. A pure culture of $L.\ bulgaricus$ containing approx. $10^8$ cells of this microorganism per ml and having a pH of 4.6 is obtained.

20 μg/ml rennet lysozyme are added to the culture which is then incubated for 12 h at 25° C.

An immunostimulant is thus obtained which contains per ml the N-acetyl muramyl peptides derived from the peptidoglycans from the walls of $10^8$ cells of $L.\ bulgaricus$ by hydrolysis with rennet lysozyme.

EXAMPLE 4

A pure culture of $L.\ bulgaricus$ is prepared in the same way as described in Example 3.

1% Liquid rennet itself containing approximately 4% lysozyme is added to the culture which is then incubated for 8 h at 20 C.

An immunostimulant is thus obtained which contains per ml the N-acetyl muramyl peptides derived from the peptidoglycans from the walls of $10^8$ cells of $L.\ bulgaricus$ by hydrolysis with rennet lysozyme.

EXAMPLE 5

A cow's milk is inoculated with 5% by volume of a mixed seed culture containing per ml approximately $5.10^7$ cells of $Lactobacillus\ bulgaricus$ and approximately $2.10^8$ cells of $Streptococcus\ thermophilus$ obtained from commercially available cultures. A yoghurt containing approximately 2.10$^7$ *L. bulgaricus* cells and approximately 10$^8$ *S. thermophilus* cells per ml is obtained after incubation for 3 h at 43° C.

50 μg rennet lysozyme are added to this yoghurt per ml. The yoghurt is then incubated for 12 h at 25° C. and cooled to 4° C.

A product of the yoghurt type having the properties of an immunostimulant is thus obtained, containing per ml the N-acetyl muramyl peptides derived from the peptidoglycans from the walls of 2.10$^7$ *L. bulgaricus* cells by hydrolysis with rennet lysozyme.

EXAMPLE 6

A yoghurt is obtained in the same way as described in Example 5. 1% Liquid rennet containing 4% lysozyme is added to this yoghurt which is then incubated for 24 h at 25° C.

A product of the yoghurt type having the properties of an immunostimulant is thus obtained, containing per ml the N-acetyl muramyl peptides derived from the peptidoglycans from the walls of 2.10$^7$ *L. bulgaricus* cells by hydrolysis with rennet lysozyme.

EXAMPLE 7

The product obtained in Example 6 is centrifuged and the whey is collected. The whey itself represents an immunostimulant rich in N-acetyl muramyl peptides derived from peptidoglycans from the cell walls of *L. bulgaricus* by hydrolysis with rennet lysozyme.

EXAMPLE 8

A sweet whey from cheese production is inoculated with a seed culture of *Lactobacillus bulgaricus* and then incubated for 6 h at 42° C.

After cooling to 25° C., 1% rennet itself containing 4% lysozyme is added, followed by incubation for 18 h at 25° C.

The immunostimulant thus obtained is rich in N-acetyl muramyl peptides derived from peptidoglycans from the cell walls of *L. bulgaricus* by hydrolysis with rennet lysozyme.

We claim:

1. A process for preparing an immunostimulant milk-based product comprising:
   adding a lysozyme to a culture of *L. bulgaricus* at a pH of from 4 to 8, incubating the culture to hydrolyze peptidoglycans of cell walls of the *L. bulgaricus*, and then collecting a suspension containing the lysozyme-treated *L. bulgaricus*;
   centrifuging the suspension to obtain a supernatant and collecting the supernatant; and
   adding the supernatant to a whey product or a fermented milk to obtain an immunostimulant milk-based product.

2. A process according to claim 1 further comprising filtering the supernatant through a membrane before adding the supernatant to the whey product or fermented milk.

3. An immunostimulant product obtained from the process of claim 1.

4. An immunostimulant product obtained from the process of claim 2.

5. A process for obtaining an immunostimulant composition comprising:
   inoculating a culture medium with *L. bulgaricus* and then incubating the culture medium for from 3 hours to 6 hours at a temperature of from 37° C. to 45° C. to obtain a culture of *L. bulgaricus*;
   adding a lysozyme to the culture of *L. bulgaricus* at a pH of from 4 to 8, incubating the culture to hydrolyze peptidoglycans of cell walls of the *L. bulgaricus*, and then collecting a suspension containing the lysozyme-treated *L. bulgaricus*; and
   centrifuging the suspension to obtain a supernatant and collecting the supernatant to obtain an immunostimulant composition.

6. A process according to claim 5 wherein the culture medium is a synthetic culture medium.

7. A process according to claim 6 wherein the synthetic culture medium is a MRS medium.

8. A process according to claim 5 wherein the culture medium is a milk-based culture medium.

9. A process according to claim 8 wherein the milk-based culture medium is a member selected from the group consisting of skimmed milk, unskimmed milk, whey, and ultrafiltration permeate.

10. A process according to claim 5 wherein the inoculated culture medium is incubated with lysozyme for from 1 hour to 48 hours at a temperature of from 15° C. to 37° C.

11. A process according to claim 5 wherein lysozyme is added to the culture of *L. bulgaricus* in an amount of from 1 μg to 500 μg lysozyme per ml of culture.

12. A process according to claim 5 wherein the lysozyme is a rennet which contains lysozyme or a lysozyme derived from rennet.

13. A process according to claim 12 wherein the lysozyme is a lysozyme derived from rennet in purified form.

14. A process according to claim 12 wherein the culture of *L. bulgaricus* is incubated with lysozyme at a pH of from about 4 to about 6.

15. A process according to claim 5 wherein the lysozyme is derived form egg white.

16. A process according to claim 15 wherein the culture bacteria is treated with lysozyme at a pH of from about 6 to about 8.

17. A process according to claim 5 further comprising filtering the supernatant through a membrane to obtain an immunostimulant solution.

18. A process according to claim 17 further comprising adding the solution to a whey product or a fermented milk to obtain an immunostimulant milk-based product.

19. An immunostimulant product obtained from the process of claim 18.

20. A process for preparing a milk-based immunostimulant composition comprising:
   inoculating a milk-based culture medium selected from the group consisting of skimmed cow's milk and unskimmed cow's milk with *L. bulgaricus* and *Streptococcus thermophilus*;
   incubating the inoculated culture medium to culture the *L. bulgaricus* and *Streptococcus thermophilus*;
   adding a lysozyme derived from rennet or a rennet which contains lysozyme to the cultured pi L. bulgaricus and *Streptococcus thermophilus* and then incubating to hydrolyze peptidoglycans of cell walls of the *L. bulgaricus* to obtain a milk-based immunostimulant composition.

21. A process according to claim 20 further comprising centrifuging the immunostimulant composition and collecting an immunostimulant whey fraction.

22. A process according to claim 20 wherein the inoculated culture medium is incubated for form 3 hours to 6 hours at a temperature of from 37° C. to 45° C. to culture the *L. bulgaricus* and wherein the *L. bulgaricus* culture is incubated with lysozyme for from 1 hour to 48 hours at a temperature of from 15° C. to 37° C.

23. A process according to claim 20 wherein lysozyme is added to the cultured *L. bulgaricus* in an amount of from 1 μg to 500 μg lysozyme per ml of culture.

24. A process according to claim 20 wherein the lysozyme is incubated with the culture of *L. bulgaricus* at a pH of from about 4 to about 6.

25. A product obtained from the process of claim 20.

26. A process for preparing a milk-based immunostimulant composition comprising:
   inoculating a culture medium selected from the group consisting of whey and ultrafiltration permeates with *L. bulgaricus*;
   incubating the inoculated culture medium to culture the *L. bulgaricus*;
   adding a lysozyme derived from rennet or a rennet which contains lysozyme to the cultured *L. bulgaricus* and then incubating to hydrolyze peptidoglycans of cell walls of the *L. bulgaricus* t obtain a milk-based immunostimulant composition.

27. A process according to claim 26 wherein the culture medium is a whey.

28. A process according to claim 26 wherein the culture medium is an ultrafiltration permeate.

29. A process according to claim 26 further comprising inoculating the culture medium with *Streptococcus thermophilus*.

30. A product obtained from the process of claim 27.

31. A product obtained from the process of claim 28.

32. A product obtained from the process of claim 29.

* * * * *

UNITED STATES PATENT AND TRADEMARK OFFICE
CERTIFICATE OF CORRECTION

PATENT NO. : 5,185,321
DATED : February 9, 1993
INVENTOR(S) : LINK, et al.

It is certified that error appears in the above-identified patent and that said Letters Patent is hereby corrected as shown below:

Column 8, line 61, delete "pi".

Column 9, line 17, "permeates" should be --permeate--.

Column 10, line 6, "t" should be --to--.

Signed and Sealed this

Ninth Day of November, 1993

Attest:

BRUCE LEHMAN

Attesting Officer

Commissioner of Patents and Trademarks